United States Patent
Nakagaki et al.

(10) Patent No.: US 7,943,024 B2
(45) Date of Patent: May 17, 2011

(54) POROUS ELECTRODE AND PROCESS OF PRODUCING THE SAME

(75) Inventors: Kunihiko Nakagaki, Nagoya (JP); Hideyuki Suzuki, Kasugai (JP); Sang Jae Lee, Ama-Gun (JP)

(73) Assignee: NGK Insulators, Ltd., Nagoya (JP)

( * ) Notice: Subject to any disclaimer, the term of this patent is extended or adjusted under 35 U.S.C. 154(b) by 1006 days.

(21) Appl. No.: 11/451,825

(22) Filed: Jun. 13, 2006

(65) Prior Publication Data

US 2006/0231397 A1    Oct. 19, 2006

Related U.S. Application Data

(63) Continuation of application No. PCT/JP2005/005433, filed on Mar. 24, 2005.

(30) Foreign Application Priority Data

Mar. 29, 2004  (JP) .................................. 2004-095670

(51) Int. Cl.
    *G01N 27/407*  (2006.01)
(52) U.S. Cl. ......... 204/424; 204/280; 204/429; 205/781
(58) Field of Classification Search ............... 204/424, 204/425, 429, 280; 205/781, 783.5
    See application file for complete search history.

(56) References Cited

U.S. PATENT DOCUMENTS

| | | | |
|---|---|---|---|
| 4,579,643 A * | 4/1986 | Mase et al. | 204/427 |
| 4,863,583 A * | 9/1989 | Kurachi et al. | 204/424 |
| 4,940,528 A * | 7/1990 | Oki et al. | 204/427 |
| 5,137,615 A * | 8/1992 | Friese et al. | 204/424 |
| 5,877,406 A * | 3/1999 | Kato | 73/23.31 |
| 5,879,525 A | 3/1999 | Kato | |
| 5,948,963 A * | 9/1999 | Kato et al. | 73/23.2 |
| 6,355,152 B1 | 3/2002 | Kato et al. | |
| 6,365,036 B1 | 4/2002 | Polikarpus | |
| 6,712,945 B2 * | 3/2004 | Diehl | 204/424 |

(Continued)

FOREIGN PATENT DOCUMENTS

DE    199 06 306 A1    9/2000

(Continued)

OTHER PUBLICATIONS

N.M. Winslow, et al., "An Instrument for the Measurement of Pore-Size Distribution by Mercury Penetration," ASTM Bulletin, The Society, Philadelphia, PA, Feb. 1, 1959, pp. 39-44.

*Primary Examiner* — Kaj K Olsen
(74) *Attorney, Agent, or Firm* — Burr & Brown

(57) ABSTRACT

A technology which makes it possible to prolong the service life of a porous electrode constituted by a sintered body of an electrode metal material and a ceramic material, and the service life of an NOx sensor element having the porous electrode. The porous electrode is produced so as to have a total pore volute of at least 0.013 ml/g and a peak pore diameter of at least 0.31 μm as measured by mercury penetration method, by a process wherein a composition which includes the electrode material and the ceramic material and to which a vanishable solid material that vanishes by firing is formed into a thin film, which is then fired to form the sintered body which consists of the electrode material and the ceramic material and which has a multiplicity of pores formed as a result of vanishing of the vanishable solid material.

4 Claims, 6 Drawing Sheets

U.S. PATENT DOCUMENTS

| | | | |
|---|---|---|---|
| 6,770,180 B1 * | 8/2004 | Diehl | 204/424 |
| 6,888,109 B2 * | 5/2005 | Heimann et al. | 219/484 |

FOREIGN PATENT DOCUMENTS

| | | |
|---|---|---|
| JP | 57-050650 A1 | 3/1982 |
| JP | 04-166757 A1 | 6/1992 |
| JP | 8-247995 | 9/1996 |
| JP | 2000-028576 A1 | 1/2000 |
| JP | 2002-098666 A1 | 4/2002 |
| JP | 2002-175814 A1 | 6/2002 |

* cited by examiner

US 7,943,024 B2

POROUS ELECTRODE AND PROCESS OF PRODUCING THE SAME

This application is a continuation of the International Application No. PCT/JP2005/005433, filed Mar. 24, 2005, which claims the benefit under 35 U.S.C. § 119(a)-(d) of Japanese Application 2004-095670, filed Mar. 29, 2004, the entireties of which are incorporated herein by reference.

TECHNICAL FIELD

The present invention relates to a porous electrode and a process of producing the same, and an electrochemical cell and an NOx sensor element which include such a porous electrode, and more particularly to a porous electrode formed of a sintered mixture (cermet) of an electrode metal material and a ceramic material, in particular, a novel structure of such a porous electrode which permits a prolonged service life of the porous electrode when used in an electrochemical cell and an NOx sensor element, and a process suitable for producing the porous electrode having such a novel structure.

BACKGROUND OF THE INVENTION

There have been proposed electrodes of various structures and compositions for use in various types of electric devices, electronic devices and electrochemical devices. In particular, there is known, as one of such kinds of electrodes, a so-called "porous electrode" (cermet electrode) formed of a sintered mixture (cermet) produced by sintering an electrode metal material and a ceramic material.

As well known in the art, such porous electrodes formed of an electrode metal material and a ceramic material which have respective properties not only exhibit new properties not obtained by electrodes formed solely of the electrode metal material, but also exhibit various properties according to specific combinations of various electrode metal materials and ceramic materials. The porous electrodes are used in various gas sensor elements and other detecting devices for measuring oxides or combustible gases contained in combustion gases in incinerators and industrial furnaces or contained in exhaust emissions of vehicles, or used in various types of devices such as fuel cells, depending upon the specific properties of the porous electrode.

Such porous electrodes as used in NOx sensor elements, oxygen sensor elements and any other gas sensor elements, for example, take the form of porous thin films each having a multiplicity of pores formed therein, and are utilized as measuring electrodes (detecting electrodes) for measuring desired gas components such as NOx and oxygen of a measurement gas, as disclosed in Patent Document 1. In these porous electrodes used as the measuring electrodes used in such various kinds of gas sensor elements, the desired gas components in the measurement gas flow through the multiple pores and come into contact with the electrode metal material within the porous electrode structure. However, this porous electrode structure has a risk of suffering from such defects as described below.

Namely, the porous electrode used, for example, as the measuring electrode in the gas sensor elements, has repeated volumetric changes caused by expansion/contraction of the electrode metal material and ceramic material during repeated measurements of the desired gas components or due to a change of the temperature of the desired gas components. The electrode metal material and the ceramic material have different amounts of change of their volumes due to different ratios of the volumetric change caused by the temperature change, so that the porous electrode structure is subject to a stress generated therein. It is also noted that the electrode metal material has a volumetric change caused by its expansion/contraction due to oxidization/reduction of the electrode metal material by oxidizing components or reducing components contained in the measurement gas. This volumetric change of the electrode metal material also causes a stress to be generated in the electrode structure. Such stresses generated within the porous electrode structure give rise to a risk of cracking of the ceramic material bonded to the electrode metal material, or a risk of removal of the electrode structure as a whole from a solid electrolyte body, which may disable the porous electrode to serve its function.

Where the porous electrode is covered by a protective layer formed thereon to protect the porous electrode, the stresses generated as described above may cause cracking of the protective layer as well.

Patent Document 1: JP-2000-28576 A

SUMMARY OF THE INVENTION

The present invention was made in view of the background art described above. It is an object of this invention to provide a porous electrode having a structure which is improved to eliminate or reduce a risk of stresses generated therein due to a volumetric change of its electrode metal material, thereby preventing various defects caused by the stresses, and to effectively prolong the service life of the porous electrode. It is another object of the present invention to provide a process suitable for producing such a porous electrode having excellent properties. It is a further object of the invention to provide an electrochemical cell or an NOx sensor element which utilizes such a porous electrode and wherein the porous electrode is kept in a stable operating state for an effectively prolonged period of time.

The object described above with respect to a porous electrode can be achieved according to a first form of the present invention, which provides a porous electrode constituted by a sintered body in the form of a thin film which consists of an electrode metal material and a ceramic material and which has a multiplicity of pores formed therein, the porous electrode being characterized by a total pore volume of at least 0.013 ml/g and a peak pore diameter of at least 0.31 μm, as measured by a mercury penetration method. The term "total pore volume" used herein is interpreted to mean a total value of volumes of the pores (amount of penetration of mercury per unit mass) obtained from a distribution of the diameters of the pores as measured by the known mercury penetration method, and the term "peak pore diameter" used herein is interpreted to mean a value of the diameter of the pore having the largest (peak) volume.

According to a preferred second form of this invention, the porous electrode has a thickness within a range of 10-50 μm.

In the porous electrode according to an advantageous third form of this invention, a porous protective layer constituted by a porous body in the form of a thin film is formed to cover a surface of the sintered body in the form of the thin film.

In the porous electrode according to a desirable fourth form of the present invention, the above-described porous protective layer in the form of the thin film has a thickness within a range of 20-60 μm.

According to an advantageous fifth form of this invention, the electrode metal material of the sintered body in the form of the thin film is a metallic material which can be easily oxidized.

The object described above with respect to an electrochemical cell can be achieved according to a sixth form of the present invention, which provides an electrochemical cell wherein a porous electrode having a structure as described above is formed on a solid electrolyte body.

The technical object described above with respect to an NOx sensor element can be achieved according to a seventh form of this invention, which provides an NOx sensor element including an electrochemical cell wherein a measuring electrode formed of a cermet of an electrode metal material capable of reducing or decomposing an NOx component of a measurement gas and a ceramic material is formed on a solid electrolyte body, the NOx sensor element being arranged to obtain a concentration of the NOx component of the measurement gas by measuring an amount of oxygen produced by reduction or decomposition of the NOx component by the measuring electrode, the NOx sensor element being characterized in that the measuring electrode is constituted by a porous electrode having a structure as described above.

The object described above with respect to a process of producing the porous electrode can be achieved according to an eighth form of this invention, which provides a process of producing a porous electrode constituted by a sintered body in the form of a thin film which consists of an electrode metal material and a ceramic material and which has a multiplicity of pores formed therein, characterized by preparing a mixture including the electrode material and the ceramic material, adding to the mixture a vanishable solid material that vanishes by firing of the mixture, forming the mixture containing the vanishable solid material into a thin film, and then firing the thus formed thin film to form the sintered body in the form of the thin film which consists of the electrode material and the ceramic material and which has the multiplicity of pores formed therein as a result of vanishing of the vanishable solid material.

In the process according to a ninth form of the present invention, the vanishable solid material is added to the mixture including the electrode metal material and the ceramic material, in an amount of at least 5 v/v % and not larger than 60 v/v %.

In the porous electrode according to the present invention, the total pore volume and the peak pore diameter as measured by the mercury penetration method are not smaller than the specified lower limits, so that the sizes of the multiple pores formed in the entirety of the porous electrode, and a total amount of the pores are sufficiently larger than those of the pores in the conventional porous electrode, whereby the sizes and total amount of the pores existing at the interface between the electrode material and the ceramic material are sufficiently larger than those of the pores existing at the interface in the conventional porous electrode.

In the porous electrode described above, therefore, the pores existing at the interface between the electrode material and the ceramic material and having sufficiently large volume (total amount) and diameters (sizes) functions as a space which permits and absorbs a higher ratio of volumetric change of the electrode metal material in the porous electrode than that of the ceramic material due to a temperature change, or a volumetric change of the electrode metal material due to a chemical reaction such as oxidization/reduction, thereby effectively preventing or minimizing the generation of stresses in the porous electrode due to the volumetric change of the electrode metal material.

Accordingly, the porous electrode according to this invention is effectively protected against cracking of the ceramic material bonded (by sintering) to the electrode metal material, or removal of the porous electrode as a whole from the member to which the porous electrode is bonded, which cracking and removal would otherwise take place due to stresses generated in the porous electrode by the volumetric change of the electrode metal material, and which would make it difficult or impossible to continue the use of the porous electrode. Thus, the service life of the porous electrode can be effectively prolonged.

In the second form of this invention, the porous electrode is a thin film having a thickness within a range of 10-50 μm, but maintains the excellent properties described above, namely, is effectively protected against various defects caused by the stresses generated in the porous electrode by the volumetric change of the electrode metal material. The porous electrode is advantageously kept in a stable operating state for a longer period of time.

In the porous electrode according to the third form of this invention, the porous protective layer constituted by the porous body in the form of a thin film is formed to cover the surface of the sintered body in the form of the thin film, so that the generation of the stresses in the porous electrode due to the volumetric change of the electrode metal material is advantageously prevented or minimized as described above, so that the porous electrode is effectively protected against cracking of the porous protective layer in the form of the thin film. Accordingly, the service life of the porous protective layer formed on the surface of the porous electrode, and the service life of the porous electrode can be more advantageously prolonged.

In the fourth form of this invention, wherein the porous protective layer has a thickness within a range of 20-60 μm, the porous electrode is more stably and advantageously protected by the porous protective layer.

In the porous electrode according to the fifth form of the invention, the electrode metal material of the porous electrode is a metallic material which can be easily oxidized, and is easily subject to a volumetric change due to oxidization/reduction, but is advantageously protected against the generation of stresses in the porous electrode due to the volumetric change of the electrode metal material, and the various defects caused by the generated stresses, whereby the service life of the porous electrode can be advantageously prolonged.

In the electrochemical cell according to the sixth form of the present invention, the porous electrode having the structure as described above is formed on the solid electrolyte body, so that the service life of the porous electrode can be advantageously prolonged, and the electrochemical cell is kept in a stable operating state for a longer period of time.

In the NOx sensor element according to the seventh form of this invention, wherein the porous electrode having the structure as described above and the prolonged service life is utilized as the measuring electrode for measuring the desired gas component of the measurement gas, so that the desired gas component can be stably measured with high accuracy for a longer period of time.

In the process of producing a porous electrode according to the eighth form of this invention, the mixture which includes the electrode metal material and the ceramic material and to which the vashiable solid material has been added is formed into a thin film, which is fired to form a sintered body in the form of a thin film which consists of the electrode metal material and the ceramic material and which has a multiplicity of pores formed therein as a result of vanishing of the vanishable solid material. Accordingly, the total amount and sizes of the multiple pores formed in the sintered body can be adjusted according to the amount and size of the vanishable solid material.

Accordingly, the process of the present invention enables the porous electrode to have the total pore volume and peak pore diameter (as measured by the mercury penetration method) not smaller than the specified lower limits described above, by simply adjusting the amount and size of the vanishable solid material to be added to the mixture.

Therefore, the process of producing the porous electrode according to the present invention permits easy and stable production of the porous electrode having an effectively prolonged service life.

In the process according to the ninth form of the present invention, the vanishable solid material is added to the mixture including the electrode metal material and the ceramic material, in an amount of at least 5 v/v % and not larger than 60 v/v %, so that the porous electrode can be stably produced such that its total pore volume and peak pore diameter as measured by the mercury penetration method are not smaller than the specified lower limits described above, whereby the porous electrode is stably given a prolonged service life.

NOMENCLATURE OF REFERENCE SIGNS

10: Solid electrolyte body; 14: First internal space; 18: Second internal space; 20: Reference air inlet passage; 22: First solid electrolyte portion; 24: Inner pumping electrode; 26: Outer pumping electrode; 28: Main pumping cell; 30: Second solid electrolyte portion; 32: Measuring electrode; 34: Reference electrode; 36: Measuring pumping cell; 40: Oxygen-partial-pressure detecting cell; 50: Rh phase; 52: $ZrO_2$ phase; and 54: Pores.

To further clarify the present invention, there will be described in detail an arrangement of a porous structure of the present invention, by reference to the drawings.

Figure 1:
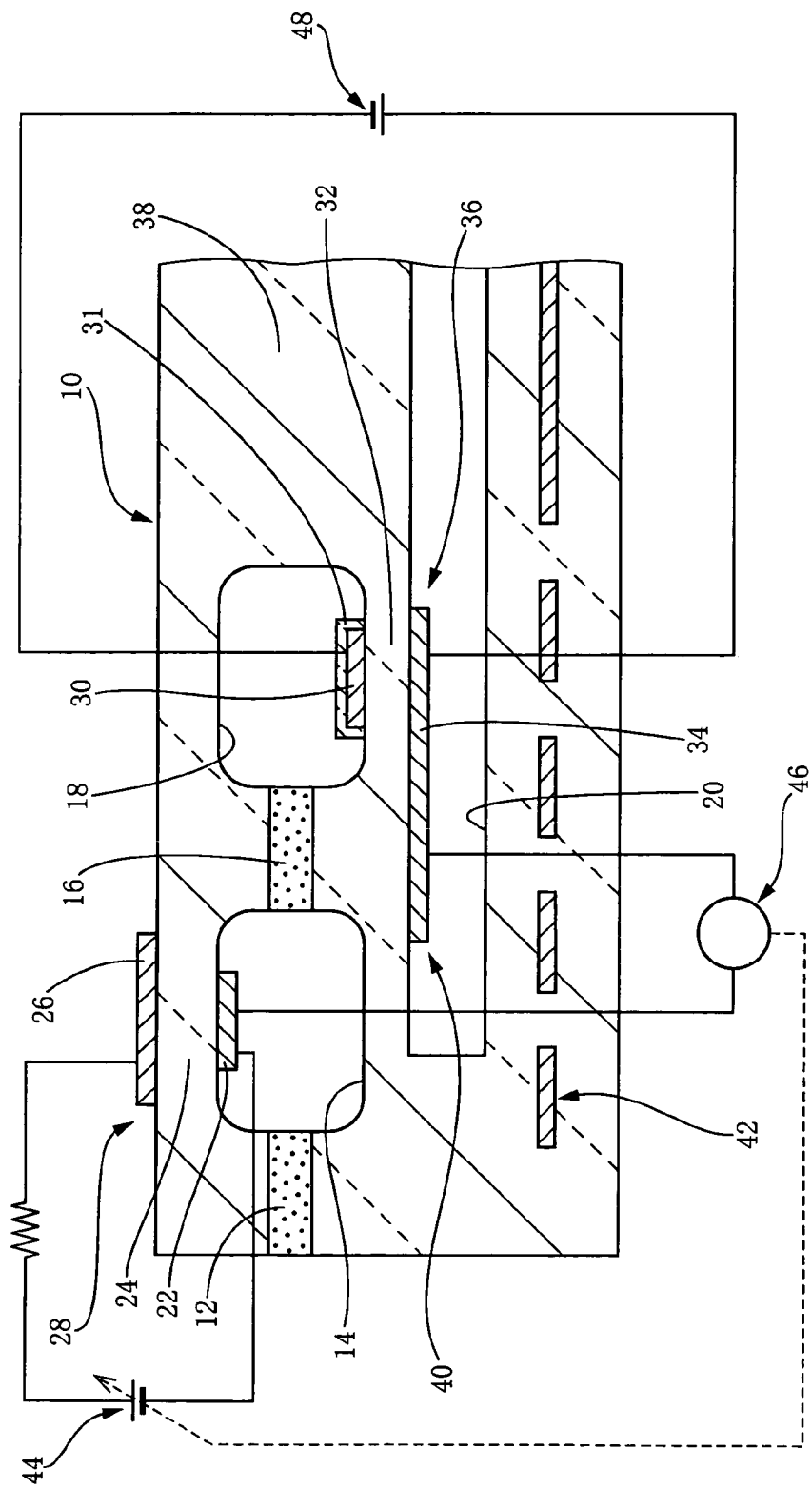
FIG. 1 is a cross sectional view schematically showing an example of an NOx sensor element according to the present invention.

Referring first to FIG. 1, there is schematically shown an internal structure of an NOx sensor element including one example of a porous electrode having a structure according to this invention. As is apparent from this figure, the NOx sensor element in this embodiment has a structure known in the art for measuring the concentration of an NOx in a measurement gas.

In FIG. 1, reference sign 10 denotes a solid electrolyte body which gives a body of the NOx sensor element, and which is formed of an oxygen-ion conductive solid electrolyte such as $ZrO_2$. In a distal end portion of this solid electrolyte body 10, there is formed a first internal space 14 which communicates with an external space through a first diffusion restricting portion 12. The solid electrolyte body 10 also has a second internal space 18 which communicates with the first internal space 14 through a second diffusion restricting portion 16. In this arrangement, a measurement gas existing in the external space is introduced into the first internal space 14 through the first diffusion restricting portion 12 under a predetermined diffusion resistance, and an atmosphere (measurement gas) in the first internal space 14 is introduced into the second internal space 18 through the second diffusion restricting portion 16 under a predetermined diffusion resistance.

In the solid electrolyte body 10, there is also formed a reference-air inlet passage 20 in the form of a space independent of the first and second internal spaces 14, 18 and extending in a longitudinal direction of the solid electrolyte body 10. This reference-air inlet passage 20 is open to the atmosphere at its proximal end portion of the solid electrolyte body 10, so that a reference air is introduced into the reference-air inlet passage 20.

The solid electrolyte body 10 having the first and second internal spaces 14, 18 and the reference-air inlet passage 20 formed therein is easily formed in a manner as known in the prior art, for example, by laminating a plurality of solid electrolyte layers in the form of thin films into an integral body. Those solid electrolyte layers consist of a plurality of solid electrolyte layers having holes and cutouts which give the internal spaces 14, 18 and the passage 20, and solid electrolyte layers which do not have such holes or cutouts and which are formed so as to sandwich each of the solid electrolyte layers having the holes and cutouts.

Within the first internal space 14 formed in the solid electrolyte body 10, there is formed an inner pumping electrode 22 in contact with a first solid electrolyte portion 24 which gives an inner surface of the first internal space 14. An outer pumping electrode 26 is formed on a surface of the first solid electrolyte portion 24 which is opposite to a surface on which the inner pumping electrode 22 is formed. These inner and outer pumping electrodes 22, 26 and the first solid electrolyte portion 24 sandwiched by and between the two pumping electrodes 22, 26 constitute a main pumping cell 28, which is an electrochemical cell.

Within the second internal space 18, on the other hand, there is formed a measuring electrode 30 in contact with a second solid electrolyte portion 32 by which the second internal space 18 and the reference-air inlet passage 20 are separated from each other. An exposed surface of the measuring electrode 30 is entirely covered by a porous protective layer 31 in the form of a porous thin film of a ceramic material such as $Al_2O_3$ through which the atmosphere in the second internal space 18 flows to the measuring electrode 30 under a predetermined diffusion resistance. Within the reference-air inlet passage 20, there is formed a reference electrode 34 in contact with a surface of the second electrolyte portion 32 which is opposite to a surface on which the measuring electrode 30 is formed. The measuring electrode 30 covered by the porous protective layer 31, the reference electrode 34, and the second solid electrolyte portion 32 sandwiched by and between the electrodes 30, 34 constitute a measuring pumping cell 36, which is an electrochemical cell.

The porous protective layer 31 formed on the measuring electrode 30 preferably has a thickness within a range of about 20-60 μm, in view of a risk of cracking of the porous protective layer 31 during firing of an electrode metal material and a ceramic material to form the measuring electrode 30, if the thickness is smaller than 20 μm, and deterioration of sensitivity of the measuring pumping cell 36 to measure the NOx concentration (as described below) due to an excessively high diffusion resistance of the porous protective layer 31, if the thickness is larger than 60 μm. Most preferably, the porous protective layer 31 has a thickness of 40 μm.

It is noted that the inner pumping electrode 22 within the first internal space 14, the reference electrode 34 within the reference-air inlet passage 20, the first and second solid electrolyte portions 24, 32, and a third solid electrolyte portion 38 located between the first and second solid electrolyte portions 24, 32, constitute an electrochemical cell which functions as a controlling oxygen-partial-pressure detecting cell 40.

Each of the inner and outer pumping electrodes 22, 26 and the reference electrode 34 is a porous cermet electrode (porous electrode) in the form of a thin film formed by sintering Pt as an electrode metal material and $ZrO_2$ as a ceramic material. On the other hand, the measuring electrode 30 is a porous cermet electrode (porous electrode) in the form of a thin film which is formed by sintering a noble metal such as Rh capable of reducing or decomposing NOx, and a ceramic material such as $ZrO_2$, and which functions as a catalyst to reduce or decompose NOx. In FIG. 1, reference sign 42 denotes a heater for heating those electrodes 22, 26, 30, 34.

In the NOx sensor element described above, a predetermined voltage is applied from a variable power source 44 between the two electrodes 24, 26 of the main pumping cell 28, so that an electric current flows between these two electrodes 24, 26 in a predetermine direction, whereby oxygen in the atmosphere (measurement gas) within the first internal space 14 is pumped out into the external measurement gas space, or the oxygen in the external measurement gas space is pumped into the first internal space 14. A suitable potentiometer 46 is provided to measure an electromotive force produced between the two electrodes 22, 34 of the controlling oxygen-partial-pressure detecting cell 40, on the basis of a difference between the oxygen concentration of the atmosphere within the first internal space 14 and the oxygen concentration of the reference air within the reference-air inlet passage 20. Further, a predetermined voltage is applied from a constant-voltage power source 48 between the two electrodes 30, 34 of the measuring pumping cell 36, so that the oxygen in the atmosphere (measurement gas) within the second internal space 18 is pumped into the reference-air inlet passage 20.

In the NOx sensor element constructed as described above, the oxygen is pumped into and from the first internal space 14 by an oxygen pumping action of the main pumping cell 28, and the voltage of the variable power source 44 is controlled on the basis of the oxygen partial pressure in the atmosphere within the first internal space 14, which is detected by the controlling oxygen-partial-pressure detecting cell 40, so that the oxygen partial pressure in the atmosphere within the first internal space 14 is controlled to a predetermined value at which the reduction of NOx is not possible. The atmosphere in the first internal space 14 the oxygen partial pressure of which is thus controlled is introduced into the second internal space 18 through the second diffusion restricting portion 16, and the NOx in the atmosphere within the second internal space 18 is reduced by the measuring electrode 30 functioning as the catalyst to reduce or decompose the NOx. The oxygen produced as a result of reduction of the oxygen is pumped out from the second internal space 18 into the reference-air inlet passage 20, by an oxygen pumping action of the measuring pumping cell 36. Since the oxygen partial pressure (oxygen concentration) in the atmosphere within the first internal space 14 is controlled to the predetermined value during this pumping action, an amount of a pumping current flowing between the measuring electrode 30 and the reference electrode 34 of the measuring pumping cell 36 is proportional to the NOx concentration.

In the present NOx sensor element, the amount of the pumping current flowing through the measuring pumping cell 36 is measured, and the NOx concentration in the measurement gas is obtained on the basis of the measured amount of the pumping current.

In the NOx sensor element in the present embodiment, each of the inner and outer pumping electrodes 22, 26, reference electrode 34 and measuring electrode 30 that are formed on the solid electrolyte body 10 is a porous cermet electrode having a multiplicity of pores formed within a sintered body in the form of a thin film consisting of an electrode metal material such as Pt or Rh and a ceramic material surface as $ZrO_2$, as described above. Of these four electrodes 22, 26, 30, 34, the measuring electrode 30 of the measuring pumping cell 36 has a specific structure not found in the conventional NOx sensor element.

Figure 2:
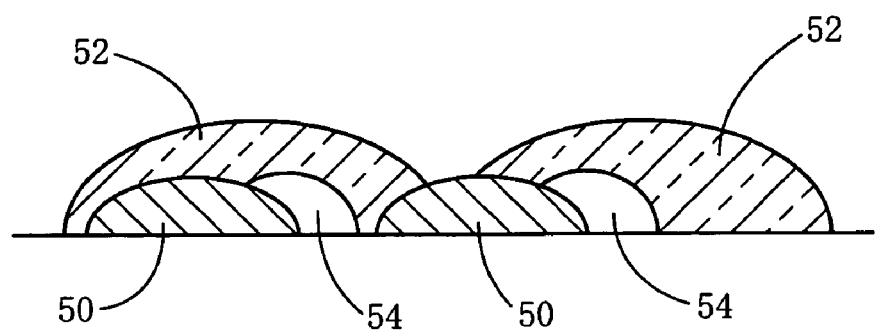
FIG. 2 is a view illustrating an internal structure of a porous electrode according to the present invention, which is provided in the NOx sensor element shown in FIG. 1.

Namely, the measuring electrode 30 in the form of a porous cermet electrode provided in the NOx sensor element of the present embodiment has an internal structure which includes Rh phases 50 formed of Rh used as the electrode metal material, and $ZrO_2$ phases 52 formed of $ZrO_2$ used as the ceramic material, and which has a multiplicity of pores 54 formed at the interface between the Rh and $ZrO_2$ phases 50, 52 bonded together, and within the $ZrO_2$ phases 52, as is apparent from FIG. 2 illustrating a part of the internal structure of the measuring electrode 30. The sizes (diameters) of the multiple pores 54 existing in the measuring electrode 30, and a total amount (total volume) of the pores 50 are sufficiently larger than those of the pores existing in the porous cermet electrode provided as the measuring electrode in the conventional NOx sensor element.

The multiplicity of pores 54 which have the sufficiently large diameter and total volume and which are formed at the interface between the Rh and $ZrO_2$ phases 50, 52 bonded together to form the measuring electrode 30 and within the $ZrO_2$ phases 52 can advantageously absorb or accommodate a volumetric change of the Rh phases 50 taking place due to a temperature change of the measurement gas or oxidization/reduction of the measuring electrode 30 by the oxidizing or reducing components within the measurement gas, during measurement by the NOx sensor element of NOx in the measurement gas such as an exhaust emission or combustion gas, even where the ratio of the volumetric change of the Rh phases 50 is higher than that of the phases 52. Thus, the pores 54 are effective to prevent or minimize the generation of stresses within the measuring electrode 30 due to the volumetric change of the Rh phases 50.

For the multiple pores 54 to have the sufficiently large sizes and total volume, the measuring electrode 30 has a total pore volume of at least 0.013 ml/g and a peak pore diameter of at least 0.31 μm as measured by a mercury penetration method.

If the total pore volume and the peak pore diameter of the measuring electrode 30 are respectively smaller than 0.013 ml/g and 0.31 μm, or if one of the total pore volume and peak pore diameter is smaller than the lower limit indicated above, both or one of the total volume and the diameter of the multiple pores 54 existing at the interface between the Rh phases 50 and the $ZrO_2$ phases 50 and within the $ZrO_2$ phases 52 are/is excessively small, making it difficult to absorb the volumetric change of the Rh phases 50 of the measuring electrode 30 due to the temperature change or oxidization/reduction of the Rh phases 50.

Although the upper limits of the total pore volume and the peak pore diameter of the measuring electrode 30 are not particularly limited, the volume of the Rh phases 50 capable of reducing or decomposing NOx decreases and the ability of the measuring electrode 30 as the catalyst accordingly decreases, with an increase of the total volume of the multiple pores 54 and the diameter of each pore 54. In addition, the volumetric specific gravity of the measuring electrode 30 as a whole decreases with a result of reduction of its strength, with an increase of the total volume and diameter of the pores 54. For assuring sufficiently high catalyst ability and strength of the measuring electrode 30, the total pore volume is preferably not more than 0.053 ml/g, while the peak pore diameter is preferably not more than 1.1 m.

While the thickness of the measuring electrode 30 in the form of the cermet electrode having the characteristic pores is not particularly limited, the thickness is preferably within a range of about 10-50 μm. If the thickness of the measuring electrode 30 is larger than 50 μm, there is a risk of generation of cracks in the porous protective layer 31 formed on the measuring electrode 30, in the process of firing of the electrode metal material (Rh phases 50) and the ceramic material ($ZrO_2$ phases 52) to form the measuring electrode 30. If the thickness of the measuring electrode 30 is smaller than 10 μm, it is difficult for the measuring electrode 30 to absorb the volumetric change due to the temperature change or the oxidization/reduction of the Rh phases 50, even where the measuring electrode 30 has the total pore volume and the peak pore diameter not smaller than the specified lower limits indicated above.

Accordingly, the thickness of the measuring electrode 30 is preferably within the range of about 10-50 μm to prevent an adverse influence on the porous protective layer 31 and to effectively prevent defects arising from the stresses generated in the measuring electrode 30 due to the volumetric change of the Rh phases 50. Most preferably, the measuring electrode 30 has a thickness of 30 μm.

In the NOx sensor element of the present embodiment, the measuring electrode 30 in the form of the porous cermet electrode consisting of the Rh phases 50 and the $ZrO_2$ phases 52 bonded together (sintered together) and having the multiple pores 54 has the total pore volume and the peak pore diameter that are not smaller than the specified lower limit, making it possible to effectively prevent or minimize the generation of stresses within the measuring electrode 30, which may be caused by the volumetric change of the Rh phases 50 due to the temperature change of the measurement gas or due to the oxidization/reduction by the oxidizing or reducing components in the measurement gas.

Therefore, the present NOx sensor element is effectively protected against cracking of the $ZrO_2$ phases 52 bonded to the Rh phases 50, due to the stresses generated in the measuring electrode 30 by the volumetric change of the Rh phases 50, or removal of the measuring electrode 30 as a whole from the second solid electrolyte portion 32, which cracking and removal would prevent accurate measurement of the NOx concentration.

Accordingly, the NOx sensor element is kept in a stable operating state capable of accurate measurement of the NOx concentration in the measurement gas, for a long period of time, and has an effectively prolonged service life.

The present NOx sensor element wherein the porous protective layer 31 in the form of a thin film is formed to cover the entirety of the exposed surface of the measuring electrode 30 is also effectively protected against cracking of this porous protective layer 31 due to the generation of stress within the measuring electrode 30, since the generation of stress is prevented or minimized as described above. Accordingly, the porous protective layer 31 is kept in a stable operating state capable of functioning to protect the measuring electrode 30 and restricting the diffusion of the measurement gas to the measuring electrode 30, whereby the service life of the NOx sensor element is further prolonged.

There will be described a process of producing the porous cermet electrodes (porous electrodes) such as the measuring electrode 30, which are utilized in a gas sensor element such as the illustrated NOx sensor element and which have a structure having the total pore volume and peak pore diameter not smaller than the specified lower limits described above.

Namely, a mixture including an electrode metal material and a ceramic material is first prepared. The ceramic material to be used is not particularly limited, and is suitably selected from the materials conventionally used for a porous cermet electrode, depending upon the required properties and application of the porous cermet electrode to be produced. The ceramic material may take the form of a powder or a pellet.

Like the ceramic material, the kind of the electrode metal material is suitably determined depending upon the required properties and application of the porous cermet electrode to be produced, and may take the form of a power or a pellet. Where the porous cermet electrode is utilized as the measuring electrode 30 in the gas sensor element such as the NOx sensor element, for example, the electrode metal material is selected from among noble metal materials, such as Pd, Pt, an alloy of Rh and Pt and an alloy of Pt and Pd, as well as Rh used in the illustrated embodiment by way of example, which noble metal material are capable of reducing or decomposing a desired gas component of the measurement gas which has bound oxygen. Where the porous cermet electrode is utilized as an electrode other than the measuring electrode 30 of the gas sensor element, metallic materials other than the noble metal materials may be used.

It is not necessary to purposely avoid the use of metallic materials that can be easily oxidized, as the electrode metal materials. Where the metallic materials that can be easily oxidized are used as the electrode metal material, these metallic materials are easily oxidized within the porous cermet electrode eventually obtained, so that the porous cermet electrode is subject to a volumetric change. However, the porous cermet electrode eventually obtained has the total pore volume and peak pore diameter not smaller than the specified lower limits, for preventing or minimizing the generation of stresses due to the volumetric change, and various other defects caused by the volumetric change. That is, the use of the metallic materials that can be easily oxidized is more effective to prevent the generation of the various defects due to oxidization/reduction of the electrode metal material within the porous cermet electrode.

The proportion of the electrode metal material and the ceramic material is suitably determined depending upon the specific kinds of the electrode metal material and ceramic material used, and the required properties and application of the porous cermet electrode to be produced. Preferably, the mixture of the electrode metal material and ceramic material contains about 50-70 v/v % of the electrode metal material (volume of the electrode metal material/volume of the ceramic material=within an approximate range between 50:50 and 70:30).

If the content of the electrode metal material in the mixture of the electrode metal material and the ceramic material is lower than 50 v/v %, the porous cermet electrode eventually obtained lacks the electrode metal material, and has a risk of accordingly deteriorated performance (properties) and other defects such as a loss of its function as the catalyst to reduce or decompose NOx. If the content of the electrode metal material is higher than 70 v/v %, the porous cermet electrode eventually obtained lacks the ceramic material, and has a risk of reduced strength of its adhesion (bonding) to a suitable support member such as a substrate plate.

Various known additives such as a binder may be added by suitable amounts known in the art, to the mixture of the electrode metal material and the ceramic material, which has a suitable proportion as described above.

In particular, a vanishable solid material which vanishes in the process of firing of the mixture of the electrode metal material and ceramic material, is mixed into (added to) the mixture. This vanishable solid material is mixed into the mixture, for the purpose of forming the pores within a sintered body obtained by firing the mixture, as a result of vanishing of the vanishable solid material.

Accordingly, the vanishable solid material takes the form of a powder or a pellet, for example, which occupies a predetermined volume in the mixture to which the vanishable solid material has been added. The kind of the vanishable solid material is not particularly limited, provided the vanishable solid material vanishes by combustion, melting or vaporization in the process of firing of the mixture. The vanishable solid materials which meet this requirement include a powder or pellet of theobromine, for instance.

The vanishable solid material may be added to the mixture of the electrode metal material and the ceramic material, at any time, for example, when or after the electrode metal material and the ceramic material are mixed together. Alternatively, the vanishable solid material may be added to one of the electrode metal material and ceramic material.

Although the amount of addition of the vanishable solid material with respect to the mixture of the electrode metal material and the ceramic material is not particularly limited, it is preferred that the vanishable solid material is present in the mixture in an amount of at least 5 v/v % and not larger than 60 v/v %.

If the amount of addition of the vanishable solid material is smaller than 5 v/v %, the diameter and the total pore volume of the pores formed as a result of vanishing of the vanishable solid material by firing of the mixture including the vanishable solid material are excessively small due to a shortage of the vanishable solid material, so that the porous cermet electrode eventually obtained is less likely to have a total pore volume and a peak pore diameter not smaller than the specified lower limits described above.

If the amount of addition of the vanishable solid material is larger than 60 v/v %, the porous cermet electrode eventually obtained lacks the electrode metal material, and has a risk of accordingly deteriorated performance (properties) and other defects such as a loss of its function as the catalyst to reduce or decompose NOx where the porous cermet electrode is utilized as the measuring electrode of the NOx sensor element.

Therefore, the amount of addition of the vanishable solid material with respect to the mixture of the electrode metal material and the ceramic material is preferably at least 5 v/v % and not larger than 60 v/v %, for assuring a sufficiently high performance of the porous cermet electrode to be produced, and for increasing its total pore volume and the peak pore diameter to values not smaller than the specified lower limits, to prevent or minimize the generation of stress due to the volumetric change of the electrode metal material within the porous cermet electrode, and various other defects caused by the volumetric change.

After the mixture which includes the electrode metal material and the ceramic material and to which the vanishable solid material has been added is prepared, this mixture is formed into a thin film, by a known method, and the thus formed thin film of the mixture is introduced into a suitable firing furnace and fired therein at a suitable temperature, in a manner known in the art, so that the vanishable solid material included in the formed thin film is burned out.

Thus, a sintered body consisting of the electrode metal material and the ceramic material is formed, and a multiplicity of pores are formed as a result of vanishing of the vanishable solid material, at the interface between the electrode metal material (electrode metal phases) and the ceramic material (ceramic phases) within the sintered body, and in the ceramic material (ceramic phases), so that the desired porous cermet electrode is obtained with its total pore volume of at least 0.013 m./g and its peak pore diameter of at least 0.31 µm, as measured by the mercury penetration method.

As described above, the porous cermet electrode having the total pore volume and peak pore diameter not smaller than the specified lower limits as measured by the mercury penetration method can be easily produced, by implementing the same process steps used to produce the conventional porous cermet electrode, except for the additional step of adding the vanishable solid material by a suitable amount to the mixture which includes the electrode metal material and the ceramic material and which is prepared to produce the desired porous cermet electrode.

In the present embodiment described above, the porous cermet electrode having a prolonged service life can be produced with extreme ease and high stability.

While the preferred embodiment of the present invention has been described above in detail, for illustrative purpose only, it is to be understood that the present invention is not limited by the foregoing description of the preferred embodiment.

In the NOx sensor element according to the illustrated embodiment described above, the measuring pumping cell 36 is constituted by the measuring electrode 30, the reference electrode 34 and the second solid electrolyte portion 32, to measure an amount of electric current flowing through the measuring pumping cell 36 when the oxygen generated by reduction of NOx of the measurement gas in the second internal space 18 is pumped out by the measuring pumping cell 36 from the second internal space 18 into the reference-air inlet passage 20, and to measure the NOx concentration in the measurement gas, on the basis of the measured amount of electric current. The measuring electrode 30 of the measuring pumping cell 36 is a porous electrode (porous cermet electrode) having a structure according to the present invention. However, the NOx sensor element provided with the porous cermet electrode is not limited to the details of the illustrated embodiment.

Accordingly, an oxygen-partial-pressure detecting cell rather than the measuring pumping cell 36 may be constituted by the measuring electrode 30, the reference electrode 34 and the second solid electrolyte portion 32, to measure by a suitable potentiometer an electromotive force generated between the two electrodes 30, 34 of the oxygen-partial-pressure detecting cell, on the basis of a difference between oxygen concentration of the measurement gas in the second internal space 18 and oxygen concentration of the reference air in the reference-air inlet passage 20, during generation of oxygen by reduction of NOx of the measurement gas in the second internal space, and to measure the concentration of a desired gas component of the measurement gas on the basis of the measured electromotive force. The measuring electrode 30 provided in this oxygen-partial-pressure detecting cell of the NOx sensor element may be a porous electrode having a structure according to the present invention.

Namely, the porous electrode having the structure according to the present invention may be provided in an NOx sensor element of any known arrangement, provided the NOx sensor element includes an electrochemical cell wherein a measuring electrode formed of a cermet including a ceramic material and an electrode metal material capable of reducing or decomposing NOx components of the measurement gas is formed on a suitable solid electrolyte body, so that the concentration of the NOx components of the measurement gas is obtained by measuring the amount of oxygen generated by reduction or decomposition of the NOx components by the measuring electrode.

All of the porous electrodes provided on the NOx sensor element according to the illustrated embodiment may be constituted by porous electrodes each having a structure according to the present invention. In this case, each of the three electrodes, that is, the inner and outer pumping electrodes 22, 26 and the reference electrode 34, has a total pore volume of at least 0.013 ml/g and a peak pore diameter of at least 0.31 μm as measured by the mercury penetration method.

In the illustrated embodiment, the principle of the present invention is applied to the electrochemical cell and the porous electrodes. However, the present invention is equally applicable to electrochemical cells and porous electrodes provided on any gas sensor elements other than the NOx sensor element, various sensor elements, and various other electric, electronic and electrochemical devices.

It is to be understood that the present invention may be embodied with various other changes, modifications and improvements not illustrated herein, which may occur to those skilled in the art and which are within the scope of the present invention, without departing from the sprit of the present invention.

EXAMPLES

While the following typical examples of this invention will further clarify the invention, it is needless to say that the present invention is not limited to these examples.

Example 1

Initially, a powder of a Pt—Rh alloy used as the electrode metal material, a powder of $ZrO_2$ used as the ceramic material, and a powder of theobromine used as the vanishable solid material were prepared by respective amounts.

Then, the powder of the Pt—Rh alloy and the powder of $ZrO_2$ were mixed together to prepare six masses (having the same composition) of a mixture (an electrode paste) of those two powders. The content of the Pt—Rh alloy powder was 60 v/v %. Subsequently, a powder of theobromine was added to and mixed with the six masses of the mixture, by respective amounts (from 5 v/v % to 60 v/v %) with respect to the mixture, as indicated in TABLE 1 given below, to prepare six kinds of an electrode composition which have respective different contents of theobromine.

Then, the six kinds of the electrode composition were formed into six thin films each of which was fired in a firing furnace at 1365° C., so that the theobromine component within the fired thin film were burned out. Thus, there were formed six kinds of a sintered body consisting of the Pt-Rh alloy and $ZrO_2$, each kind having a multiplicity of pores formed as a result of burning of theobromine. That is, six porous electrodes (porous cermet electrodes) in the form of thin films were formed from the respective electrode materials having the following respective different amounts of addition of theobromine to the mixture including the Pt—Rh alloy and $ZrO_2$; 5 v/v %, 10 v/v %, 20 v/v %, 40 v/v %, 50 v/v % and 60 v/v %. These six porous electrodes are respectively referred to as Sample 1, Sample 2, Sample 3, Sample 4, Sample 5 and Sample 6.

For comparison, there was prepared an electrode material consisting of the Pt—Rh powder and $ZrO_2$ powder having the same proportion as the electrode materials of the porous electrodes of Samples 1-6 but not including theobromine. This electrode material was formed into a thin film, which was fired into a sintered body, under the same conditions as the thin films from which the porous electrodes of Samples 1-7 were formed. Thus, a porous electrode (Sample 7) was prepared from the sintered body of the electrode material not including theobromine.

The total pore volume and the peak pore diameter of each of the porous electrodes of Samples 1-7 were measured in accordance with JIS R 1655. The measured values are also indicated in TABLE 1 below.

TABLE 1

|  | Theobromine Content (v/v %) | Total Pore Volume (ml/g) | Peak Pore Diameter (μm) |
| --- | --- | --- | --- |
| Sample 1 | 5 | 0.013 | 0.31 |
| Sample 2 | 10 | 0.014 | 0.34 |
| Sample 3 | 20 | 0.017 | 0.43 |
| Sample 4 | 40 | 0.035 | 0.81 |
| Sample 5 | 50 | 0.047 | 0.99 |
| Sample 6 | 60 | 0.053 | 1.11 |
| Sample 7 | 0 | 0.013 | 0.29 |

It will be understood from the measured value of TABLE 1 that all of the porous electrodes of Samples 1-6 obtained from the electrode materials to which theobromine was added as the vanishable solid material have the total pore volume of at least 0.013 ml/g and the peak pore diameter of at least 0.31 μm, that is, both of the total pore volume and the peak pore diameter were not smaller than the lower limits specified according to the present invention. It will also be understood that both of the total pore volume and the peak pore diameter increase with an increase in the amount of addition of theobromine to the mixture including the Pt—Rh alloy and $ZrO_2$ (the content of the vanishable solid material in the electrode materials). On the other hand, the porous electrode of Sample 7 obtained from the electrode material to which theobromine was not added as the vanishable solid material has the total pore volume of 0.013 ml/g, that is, the total pore volume not smaller than the specified lower limit of the present invention, but has the peak pore diameter smaller than the specified lower limit of the present invention.

These facts clearly indicate that the use of the electrode material obtained by adding the vanishable solid material to the mixture including the electrode metal material and the ceramic material makes it possible to enable the produced porous electrode to have the total pore volume and the peak pore diameter which are both not smaller than the lower limits specified according to the present invention.

Example 2

Initially, there were prepared five kinds of NOx sensor elements which have the same internal structure as shown in FIG. 1 and the respective measuring electrodes (30) which are constituted by the porous electrodes of Samples 2-5 and 7 in Example 1, respectively. The prepared five NOx sensor elements the measuring electrodes (30) of which are the porous electrodes of Samples 2, 3, 4, 5 and 7 in Example 1 are respectively referred to as Sample A, Sample B, Sample C, Sample D and Sample E.

Then, the prepared five kinds of NOx sensor elements (Samples A-E) were subjected to a stress test in which the measuring electrode (30) was stressed by its expansion/contraction caused by cyclic ON-OFF operations of the main pumping cell (28), controlling oxygen-partial-pressure detecting cell (40) and measuring pumping cell (36) of each Sample. One cycle of the ON-OFF operations consists of an operation of the cells for five minutes while the NOx sensor element was held at a temperature of 700-800° C. by its heater, and a rest of the cells for the following five minutes. This stress test was conducted to purposely cause expansion/contraction of the measuring electrode (30) due to its oxidization/reduction during the cyclic ON-OFF operations of each NOx sensor element, for thereby giving stresses to the measuring electrode (30) due to its expansion/contraction.

Each of the five NOx sensor elements of Samples A-E was inspected to obtain a relationship between the number of the ON-OFF cycles and a percentage value of generation of defects of the NOx sensor elements by the stress test. This relationship is indicated in FIG. 3.

Figure 4:
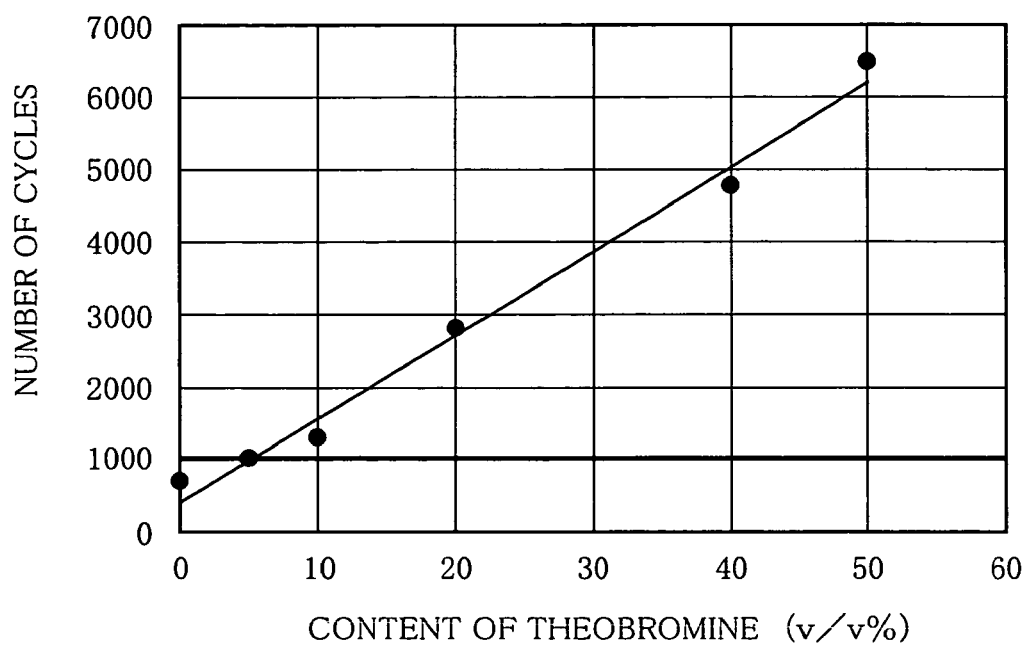
FIG. 4 is a graph indicating a relationship between the amount of addition of a vanishable solid material to a mixture including the electrode metal material and the ceramic material, and the number of the ON-OFF cycles above which the percentage value of the generation of the defects of the NOx sensor elements exceeded a predetermined threshold in the stress test conducted for the four kinds of NOx sensor elements according to the invention and the conventional NOx sensor element.
Figure 5:
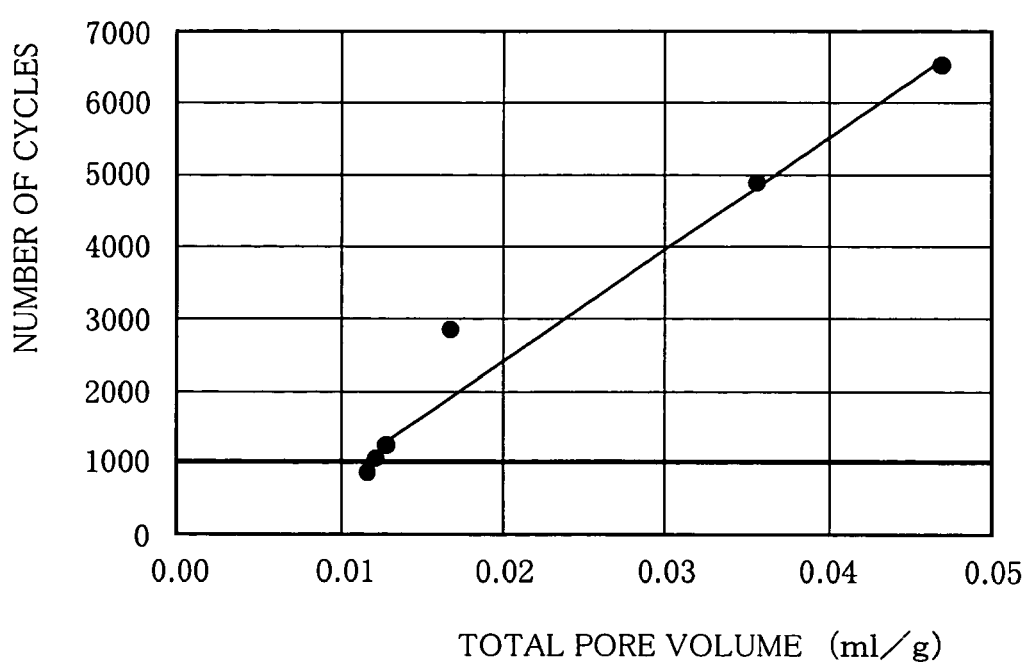
FIG. 5 is a graph indicating a relationship between the total pore volume of the porous electrode and the number of the ON-OFF cycles above which the percentage value of generation of the defects of the NOx sensor elements exceeded a predetermined threshold in the stress test conducted for the four kinds of NOx sensor elements according to the invention and the conventional NOx sensor element.
Figure 6:
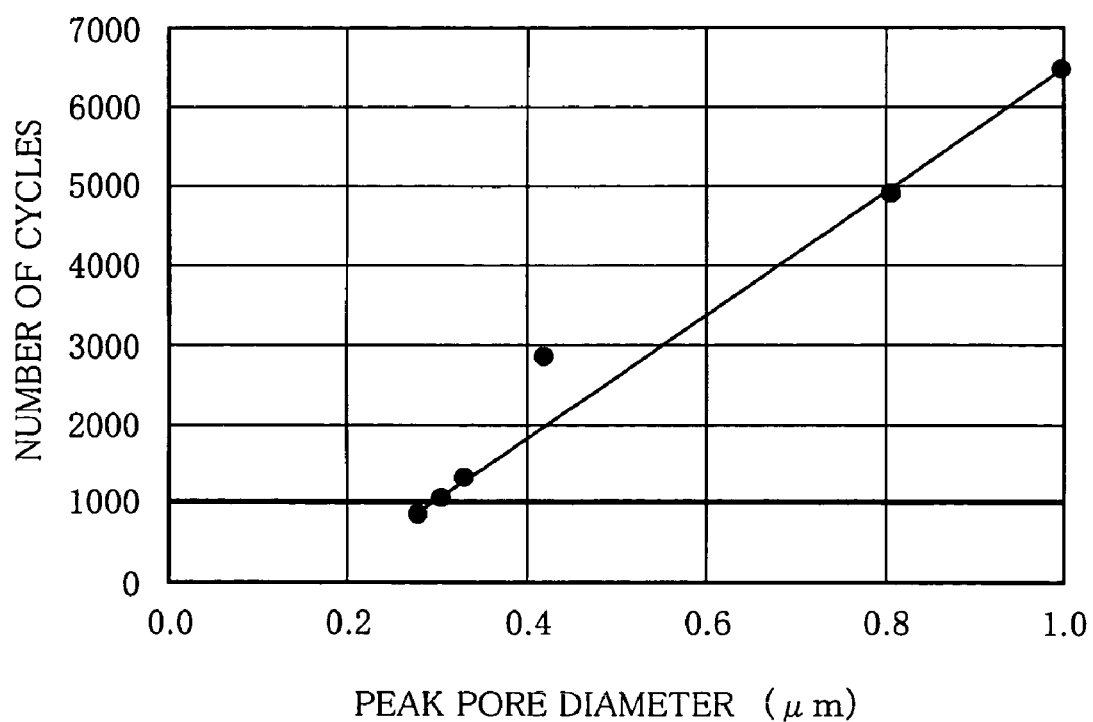
FIG. 6 is a graph indicating a relationship between the peak pore diameter of the porous electrode and the number of the ON-OFF cycles above which the percentage value of generation of the defects of the NOx sensor elements exceeded a predetermined threshold in the stress test conducted for the four kinds of NOx sensor elements according to the invention and the conventional NOx sensor element.

On the basis of the obtained relationships between the number of the ON-OFF cycles and the percentage values of generation of the defects of the NOx sensor elements, there was obtained a relationship between the amount of addition of theobromine to the mixture including the Pt-Rh alloy and $ZrO_2$, and the number of the ON-OFF cycles above which the percentage value of generation of the defects of the NOx sensor elements exceeded 0.1%. This relationship is indicated in FIG. 4. There were also obtained a relationship between the total pore volume of the measuring electrode (30), and the number of the ON-OFF cycles above which the percentage value of generation of the defects of the NOx sensor elements exceeded 0.1%, and a relationship between the peak pore diameter of the measuring electrode (30), and the number of the ON-OFF cycles above which the percentage value of generation of the defects of the NOx sensor elements exceeded 0.1%. These relationships obtained are indicated in FIGS. 5 and 6, respectively. It is generally recognized that the NOx sensor elements the number of the ON-OFF cycles of which corresponding to 0.1% of generation of the defects is 1000 or larger are capable of measuring the NOx concentration with high stability for a long period of time and have sufficiently prolonged service lives.

Figure 3:
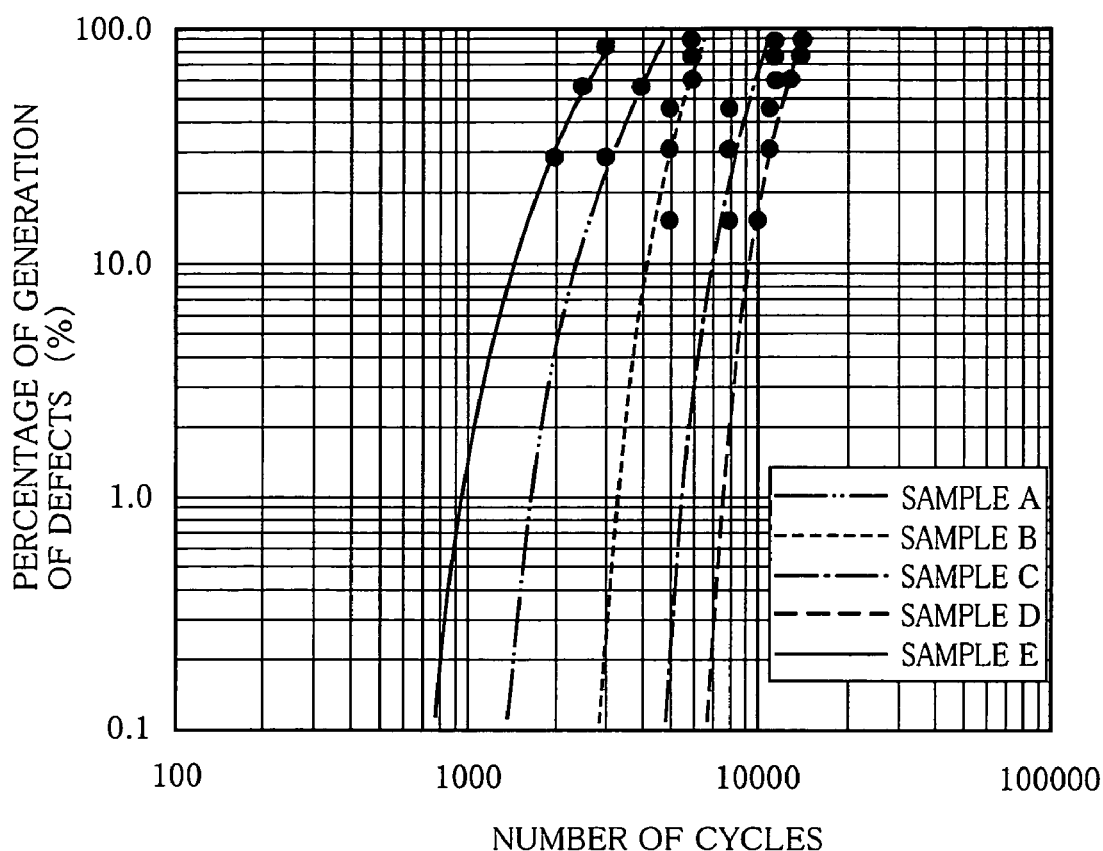
FIG. 3 is a graph indicating relationships between the number of ON-OFF cycles performed in a stress test conducted for four kinds of NOx sensor elements according to the invention and a conventional NOx sensor element, and a percentage value of generation of defects of the NOx sensor elements.

It will be understood from FIG. 3 that the NOx sensor element of Sample E having the measuring electrode (30) constituted by the porous electrode formed from the electrode material to which theobromine was not added suffered from a larger number of defects at a smaller number of the ON-OFF cycles, than the NOx sensor elements of Samples A-D having the measuring electrodes (30) constituted by the porous electrodes formed from the electrode materials to which theobromine were added.

It will be understood from FIG. 4 that the addition of theobromine to the electrode material used to form the measuring electrode (30) permits the number of the ON-OFF cycles corresponding to 0.1% of generation of the defects to exceed 1000, and that the number of the ON-OFF cycles of the ON-OFF cycles corresponding to 0.1% of generation of the defects increases with an increase of the content of theobromine in the electrode material.

It will be understood from FIGS. 5 and 6 that the number of the ON-OFF cycles corresponding to 0.1% of generation of the defects increase with an increase of the total pore volume of the measuring electrode (30) and with an increase of the peak pore diameter.

It is easily recognized from these facts that the NOx sensor elements provided with the measuring electrodes (30) formed from the electrode materials to which a vanishable solid material has been added are capable of measuring the NOx concentration with high stability for a long period of time, while on the other hand the NOx sensor elements provided with the measuring electrodes (30) formed from the electrode materials to which any vanishable solid material has not been added are almost unlikely to be capable of measuring the NOx concentration with high stability for a long period of time. It is clearly recognized that the service life of the NOx sensor is prolonged with an increase of the total pore volume of the measuring electrode (30), and with an increase of the peak pore diameter of the measuring electrode (30).

What is claimed is:

1. An NOx sensor element including an electrochemical cell, wherein a measuring electrode formed of a cermet of an electrode metal material capable of reducing or decomposing an NOx component of a measurement gas and a ceramic material is formed on a solid electrolyte body, said NOx sensor element being arranged to obtain a concentration of said NOx component of said measurement gas by measuring an amount of oxygen produced by reduction or decomposition of the NOx component by said measuring electrode, wherein an improvement comprises:

said measuring electrode being constituted by a porous electrode comprising a sintered body in the form of a thin film comprising an electrode metal material and a ceramic material and which has a multiplicity of pores formed therein, wherein an entirety of said porous electrode is porous, and wherein said sintered body has a total pore volume in a range of at least 0.017 ml/g to not more than 0.053 ml/g and a peak pore diameter in a range of at least 0.43 µm to not more than 1.1 µm, as measured by a mercury penetration method.

2. The NOx sensor element according to claim 1, wherein said porous electrode has a thickness within a range of 10-50 µm.

3. The NOx sensor element according to claim 1, wherein a porous protective layer constituted by a porous body in the form of a thin film is formed to cover a surface of said sintered body of said porous electrode.

4. The NOx sensor element according to claim 3, wherein said porous protective layer has a thickness within a range of 20-60 µm.

* * * * *